United States Patent [19]

Jacobson et al.

[11] Patent Number: 5,273,901
[45] Date of Patent: Dec. 28, 1993

[54] GENETICALLY ENGINEERED COCCIDIOSIS SPOROZOITE 21.5 KB ANTIGEN, AC-6B

[75] Inventors: James W. Jacobson, Rockville; Robert L. Strausberg, Silver Spring; Susan D. Wilson, Rockville; Sharon H. Pope, Gaithersburg; Susan L. Strausberg, Silver Spring; Michael D. Ruff, Bowie; Patricia C. Augustine, Laurel; Harry D. Danforth, Severn, all of Md.

[73] Assignee: Enzon Corp. /US. Dept. of Agriculture, S. Plainfield, N.J.

[21] Appl. No.: 581,693

[22] Filed: Sep. 12, 1990

Related U.S. Application Data

[63] Continuation-in-part of PCT/US89/02918, filed Jul. 5, 1989, which is a continuation-in-part of Ser. No. 215,162, Jul. 5, 1988, which is a continuation-in-part of Ser. No. 746,520, Jun. 19, 1985, abandoned, which is a continuation-in-part of Ser. No. 627,811, Jul. 5, 1984, abandoned.

[51] Int. Cl.⁵ .............. A61K 39/12; C07K 15/04; C12N 15/30
[52] U.S. Cl. .............. 435/243; 435/69.3; 435/320.1; 435/6; 530/388.6; 530/388.85; 536/23.7; 424/85.8; 424/88; 424/92
[58] Field of Search .......... 424/85.8, 84, 92; 435/69.3, 320.1, 71.3, 243, 6; 530/388.6, 388.85; 536/23.7

[56] References Cited

U.S. PATENT DOCUMENTS

| | | |
|---|---|---|
| 4,710,377 | 12/1987 | Schenkel et al. |
| 4,724,145 | 2/1988 | Murray et al. |
| 4,874,705 | 10/1989 | Andrews et al. |

FOREIGN PATENT DOCUMENTS

| | | |
|---|---|---|
| 0135712 | 8/1983 | European Pat. Off. |
| 0135073 | 3/1985 | European Pat. Off. |
| 0164176 | 12/1985 | European Pat. Off. |
| 0167443 | 1/1986 | European Pat. Off. |
| 0231537 | 8/1987 | European Pat. Off. |
| 0337589 | 1/1989 | European Pat. Off. |
| 0324648 | 7/1989 | European Pat. Off. |
| 0344808 | 12/1989 | European Pat. Off. |

OTHER PUBLICATIONS

Jenkins (1988) Experimental Parasitology 66: 96-107 Eimeria Acervulina: DNA Cloning & Characterization of Sporozoite.
Jenkins (1987) R. Mol. and Biochem Parasit. 25:155-164 "Identification of Immunodominant Surface Antigens of E. acerv . . . ".
Young and Davis PNAS 80: 1194-1198 (1983) Efficient Isolation of Genes by Using Antibody Probes.
Broome et al PNAS 75: 2746-2749 (1978).
McAndrews et al J Cell Biochem Suppl 10A, 149 to 1986.
Augustine et al., Avian Diseases 29(4):1212-1223 (1985).
Augustine et al., Proc. Helminthol. Soc. Wash. 54(2):207-211 (1987).
Augustine et al., Molecular Strategies of Parasitic Invasion, Alan R. Liss, Inc. pp. 511-520 (1987).
Augustine et al., J. Parasit. 74(4):653-659 (1988).
Danforth, J. Parasitol. 68(3):392-397 (1982).
Danforth et al., Poultry Science 62:2145-2151 (1983).
Danforth, Am. J. Vet. Res. 44(9):1722-1727 (1983).
Danforth et al., Fed. Proc. 44:1334 #5398 (1985).
Danforth et al., Avian Diseases 30(1):37-42 (1985).
Wisher, Mol. Biochem. Parasitology 21:7-15 (1986).

Primary Examiner—Y. Christina Chan
Assistant Examiner—T. Michael Nisbet
Attorney, Agent, or Firm—Sterne, Kessler, Goldstein & Fox

[57] ABSTRACT

This invention relates to novel recombinant antigenic proteins of avian coccidiosis, and fragments thereof containing antigenic determinants, and to the genes that encode the antigenic peptides. This invention also relates to vaccines made using the novel antigenic proteins of avian coccidiosis and to methods of immunizing chickens against avian coccidia.

4 Claims, 12 Drawing Sheets

```
5' ATGGCTGACTTCTTCAGCGGCTTAGTAGGAGGTGTCGTAGGGGCTGTTGCTGCTGTTGAT 3'
         10        20        30        40        50        60

5' GTCCCAGCAGAAGGAGAGAGACTGCCTCGGCCTGCACCCGGTACAGAATGGAGTCTATGC 3'
         70        80        90       100       110       120

5' TGTAGTAAGCTAGGAGAGAGCGGGCGGGAGCTTGAAGGCTTTGTTCAGCAGCTAACGTTT 3'
        130       140       150       160       170       180

5' ATATTAGGCAAGCTAGCTAGCTGTATGAGGGTAGGGATCGAGCATCTAAGCCGCTGTGTT 3'
        190       200       210       220       230       240

5' GCTGAAGGTAGACCGCCTTCTTCTTGTCCTTGTTTAATGAATAAGGCTGATATAGATGAG 3'
        250       260       270       280       290       300

5' GGTATAGGTGCAGGTAAACAAGGCGCTGATTATCTTATAAGAGGAGGTAAGCTTGTGCTT 3'
        310       320       330       340       350       360
```

5' ATGCCAGGGCTTCCACCGCCCGGACCCGCCTCAAAGGCTGATCGCTCAGACACGGCAGTG
       10        20        30        40        50        60

5' GCCTCCGCGGCGAGGGAGGAGGCCAGCAAGCTGCCAATCTGAATCCGACACAGGAAGTT 3'
       70        80        90       100       110       120

5' ACGACAGGTCCTACTGGGACCCAGCTTCCCAAACCCGAAGAACGTTCGGCAGAAGTAGAT 3'
       130       140       150       160       170       180

5' GAAGAGGAGAGCCTTCCCATAATGAAGCATCAGGAGCGCAGACCGTTTCGAAGAAAAAG 3'
       190       200       210       220       230       240

5' CCCAAGAAGACAAATGCGGAAGTTGACGGGCGAACATAAGCAGAAGAAGTCGCCAAAGGAG 3'
       250       260       270       280       290       300

5' GAGGACTTGGAGGCACGAAGAAGAAAAAGGAAAGAAGGAGATGCGCCGAGT 3'
       310       320       330       340       350       360

5' GAGAGATCCGGCCAACCCTCCGATGTGGAGAGCATTAACCAAGAAAATGCTGGTGAGACT 3'
       370       380       390       400       410       420

FIG. 1A

5' GTTGCAGCAGCCGATGCCGACGCCTGGATGGGGATTCGGGTTGTGTTTGGAAATAGGGAAGGA 3'
    430           440           450           460           470           480

5' ATTACTGATGCTTCTAAAAGGCATTCCGACGCACAGGATGCATCACCGTCTGCCCTCGT 3'
    490           500           510           520           530           540

5' CCCTCTCTTCTCGGGTTAATTGTCGGCTCGGACCATGCTGAGGAAACCCCAAAGGAAAC 3'
    550           560           570           580           590           600

5' GAAGTTCCCCCTTGAAACTGTCCACTGTGGACGGTGCGGATGACCAGAGGACAGTTCC 3'
    610           620           630           640           650           660

5' TCGAGTGACGACGGCGAGACGGACGGAGGTATCACCAGCACAATAGCGGGTTTCTTTTGG 3'
    670           680           690           700           710           720

5' GGAATCTAATGA
    730

FIG. 1B

```
  5                                          10                                       15                              20
MetProGlyLeuProProProAlaProAlaSerLysAlaAspArgSerAspThrAlaVal
 25                                          30                                       35                              40
AlaSerAlaAlaArgGluGluAlaGlnAlaAlaAsnLeuAsnProThrGlnGluVal
 45                                          50                                       55                              60
ThrThrGlyProThrGlyAspGlnLeuProLysProGluGluArgSerAlaGluValAsp
 65                                          70                                       75                              80
GluGluGlyGluProSerHisAsnGluAlaSerGlyAlaGlnThrValSerLysLysLys
 85                                          90                                       95                             100
ProLysLysThrAsnAlaGluValAspGlyGluHisLysGlnLysLysSerProLysGlu
105                                         110                                      115                             120
GluAspLeuGluGlyThrLysLysLysLysLysLysArgLysGlyAspAlaProSer
125                                         130                                      135                             140
GluArgSerGlyGlnProSerAspValGluSerIleAsnGlnGluAsnAlaGlyGluThr
```

FIG. 2A

```
145                 150                 155                 160
ValAlaAlaAlaAspAlaThrProGlyTrpGlyPheGlyLeuPheGlyAsnArgGluGly
165                 170                 175                 180
IleThrAspAlaSerLysArgHisSerAspAlaGlnAspAlaSerProSerAlaProArg
185                 190                 195                 200
ProSerLeuLeuGlyLeuIleValGlySerAspHisAlaGluThrProLysGlyAsn
205                 210                 215                 220
GluValProProLeuLysLeuSerThrValAspGlyAlaAspAspGlnSerAspSerSer
225                 230                 235                 240
SerSerAspAspGlyGluThrAspGlyGlyIleThrSerThrIleAlaGlyPhePheTrp
GlyIle
```

FIG. 2B

5' ATGGCTGACTTCTTCAGCGGGCTTAGTAGGAGGTGTCGTAGGGGCTGTTGCTGCTGTTGAT 3'
       10        20        30        40        50        60

5' GTCCCAGCAGAAGGAGAGAGACTGCCTCGGCCTGCACCCGGTACAGAATGGAGTCTATGC 3'
       70        80        90       100       110       120

5' TGTAGTAAGCTAGGAGAGAGCGGGGGGAGCTTGAAGGCTTGTTCAGCAGCTAACGTTT 3'
      130       140       150       160       170       180

5' ATATTAGGCAAGCTAGCTGTATGAGGGTAGGGATCGAGCATCTAAGCCGCTGTGTT 3'
      190       200       210       220       230       240

5' GCTGAAGGTAGACCGCCCTTCTTCTTGTCCTTGTTTAATGAATAAGGCTGATATAGATGAG 3'
      250       260       270       280       290       300

5' GGTATAGGTGCAGGTAAACAAGGCGCTGATTATCTTATAAGAGAGGTAAGCTTGTGCTT 3'
      310       320       330       340       350       360

FIG. 3A

5' GAGGCTCTCTTGAAGCAGCTAAGGTTGCAGCTACAAGAGGTTAATACTTGTTGAAGG 3'
    370           380          390          400        410     420

5' AGTAAGGATATTATATTAAGAAACATCCCACAGACACAAGAAAAGCTGTCTCAAGCATAC 3'
    430          440           450          460         470      480

5' AGCTCTTTCTTAAGAGGCTATGAAGGTAGCGGCAGGTCTCTAGGAGGCTATGCTCCCTTCA 3'
    490          500           510          520         530       540

5' TATCAGCAGCAGCAGCACCCTTCAAGCTACGGTGCAGCCTTCAAGCCAGCAAGCC 3'
    550          560           570          580         590    600

5' TCAGGCTTCTTCTGGTAGA 3'
    610        620

FIG. 3B

```
   5                          10                          15                          20
MetAlaAspPhePheSerGlyLeuValValGlyGlyValValGlyAlaValAlaValAsp
                            25                          30                          35                          40
ValProAlaGluGlyGluArgLeuProArgProAlaProGlyThrGluTrpSerLeuCys
                            45                          50                          55                          60
CysSerLysLeuLeuGlyGlySerGlyArgGluLeuGluGlyPheValGlnGlnLeuThrPhe
                            65                          70                          75                          80
IleLeuGlyLysLeuAlaSerCysMetArgValGlyIleGluHisLeuSerArgCysVal
                            85                          90                          95                          100
AlaGluGlyArgProProSerSerCysProCysLeuMetAsnLysAlaAspIleAspGlu
                            105                         110                         115                         120
GlyIleGlyAlaGlyLysLysGlnGlyAlaAspTyrLeuIleArgGlyGlyLysLeuValLeu
```

FIG. 4A

```
              125                    130                    135                    140
GluAlaLeuLeuGluAlaAlaAlaLysValAlaAlaAlaThrArgGlyLeuIleLeuValGluGly
              145                    150                    155                    160
SerLysAspIleIleLeuArgAsnIleProGlnThrGlnGluLysLeuSerGlnAlaTyr
              165                    170                    175                    180
SerSerPheLeuArgGlyTyrGluGlySerGlyArgSerLeuGlyGlyTyrAlaProSer
              185                    190                    195                    200
TyrGlnGlnGlnHisProSerSerTyrGlyAlaAlaProSerSerGlnGlnAla
              205
SerGlyPhePheTrp***
```

FIG. 4B

5' AGAGAAGAAGACAAAAGAGAAGAACAAAAGAGAAGAAGAAGAAGAAGAA 3'
       10        20        30        40        50        60

5' GAGAGAGGAGAAGAAGAAAAGAGAAGAGCGGCAGCACCTGCAGCAGCAACA 3'
       70        80        90       100       110       120

5' GCAGCAGCACCTGCAGCAGCAACAGCAGCTGCAACAGCAGCAGCAGCTACA 3'
      130       140       150       160       170       180

5' GCAACACCAGCTGCAGCAGCACCAGCTGCAGCAGCTGCAGCAGCAGCAGCA 3'
      190       200       210       220       230       240

5' GCAACACCAGCTGCAGCAGCACCACCAGCTGCAGCAGCCCGAGCAGGAGCA 3'
      250       260       270       280       290       300

5' GCAAAGGCAGCGGAAGCAGAGAACCGAAACAGCAGCAGCAGCAGCAAGCA 3'
      310       320       330       340       350       360

5' GAGAAAGCGAAAACACAGCAACAGCAACAACAGCAGCTGCAGCAAGAGCAGCA 3'
      370       380       390       400       410       420

5' GCAGCATCAGCAGCAGGTAAGCCTGGGGACATGCAGCAGCATCAACAGCAGCAAAAGCA 3'
      430       440       450       460       470       480

5' GCGCAGGAAAAAGCGGCGAAACGCAGCAACAGCAGCAACAGCATCAAAGGAA 3'
      490       500       510       520       530       540

5' TAA

FIG. 5

```
        5                  10                 15                 20
ArgGluGluAspLysArgGluGluAspLysArgGluGluGluGluGluArgGlu
        25                 30                 35                 40
GluArgGlyGluGluGluGluLysGluGluGluArgAlaAlaAlaProAlaAlaAlaThr
        45                 50                 55                 60
AlaAlaAlaAlaProAlaAlaAlaAlaThrAlaAlaAlaAlaThrAlaAlaAlaThr
        65                 70                 75                 80
AlaThrProAlaAlaAlaAlaAlaAlaProAlaAlaAlaAlaAlaAlaAlaAlaAla
        85                 90                 95                 100
AlaThrGlyAlaAlaAlaAlaAlaProAlaAlaAlaThrAlaAlaAlaAlaGlyAlaAlaAlaGlyAla
        105                110                115                120
AlaLysAlaAlaAlaGluAlaAlaArgThrGluThrGluGlyAlaAlaAlaAlaGlyAlaAlaAlaGluAla
        125                130                135                140
GluLysAlaAlaLysThrGlnAlaAlaAlaThrAlaAlaAlaAlaThrThrAlaAlaAlaAlaArgAlaAla
        145                150                155                160
AlaAlaSerAlaAlaGlyLysProGlyHisAlaAlaAlaAlaSerThrAlaAlaAlaLysAla
        165                170                175                180
AlaGlnGluLysAlaAlaAlaLysAlaAlaAsnAlaAlaAlaThrAlaAlaAlaThrAlaSerLysGlu
```

FIG. 6

5' CACTCCCACACTACATCAGCAGCAATACAAGCAGCAGCTGGCGCTGCCAGCAGCAGCA 3'
       10        20        30        40        50        60

5' CCGCCAGCAGCAGCACCGCCAACAGCAGCAGCCAACAGCAGCACCATCAGCAAAAAAAAA 3'
       70        80        90       100       110

FIG. 7

HisSerHisThrThrSerAlaAlaAlaAlaIleGlnAlaAlaAlaAlaAlaLeuProAlaAlaAlaAlaAla
         5              10              15              20

ProProAlaAlaAlaAlaAlaProProThrAlaAlaAlaAlaAlaProSerAlaLysLysLys
          25              30              35

FIG. 8

5' CTCATGGGGCTTCCAGGCAGAGAGAGTCCTGCTGCTTCCCCTGCTGCTGCTGCT 3'
           10        20        30        40        50      60

5' GCTGCTGCACCAGCAGCAGCAGCAGCAGAGCAGACTCGGGCCGCCGTCC 3'
          70        80        90       100       110     120

5' GGGCCGAGCAGCAGCACCCAGCTCCAGCACTACCAGCAAGACCAGCAGCAG 3'
          130       140       150       160       170     180

5' CAGCAGCAGCAGCAGCAGCAGCAGCAGGTTCTGGTCATG 3'
          190       200       210       220

FIG. 9

5                   10                  15                  20
            LeuMetGlyLeuProGlyArgGluSerProAlaAlaAlaSerProAlaAlaAlaAlaAla
                          25                  30                  35                  40
            AlaAlaAlaProAlaAlaAlaAlaAlaAlaAlaAlaAlaGluProAspSerGlyAlaAlaSer
                          45                  50                  55                  60
            GlyAlaGluGlnHisGlnLeuGlnHisGlnAspTyrGlnGlnAspGlnGlnGln
                          65                  70                  75
            GlnGlnGlnGlnGlnGlnGlnGlnGlnGlnGlnGlnValLeuValMet

FIG. 10

GENETICALLY ENGINEERED COCCIDIOSIS SPOROZOITE 21.5 KB ANTIGEN, AC-6B

CROSS-REFERENCE TO RELATED APPLICATIONS

This application is a continuation-in-part of PCT/US89/02918, filed Jul. 5, 1989, which is a continuation-in-part of U.S. patent application Ser. No. 07/215,162, filed Jul. 5, 1988; which is a continuation-in-part of U.S. patent application Ser. No. 06/746,520, filed Jun. 19, 1985, now abandoned, which is a continuation-in-part of U.S. patent application Ser. No. 06/627,811, filed Jul. 5, 1984, now abandoned.

FIELD OF THE INVENTION

This invention is in the field of avian coccidiosis and is directed to recombinant antigenic proteins of avian coccidia and to the genes that encode the proteins. These antigenic proteins may be used in a vaccine against avian coccidia.

BACKGROUND OF THE INVENTION

Coccidiosis is a disease of both invertebrates and vertebrates, including man, caused by intracellular parasitic protozoa which generally invade the epithelial cells lining the alimentary tract and the cells of associated glands. The crowded conditions under which many domestic animals are raised have contributed to increased incidence of the disease. Virtually every domestic animal is susceptible to infection, and distribution of the parasite is worldwide. Coccidiosis is therefore the cause of significant economic loss throughout the world.

The poultry industry suffers particularly severe losses, with coccidiosis being the most economically important parasitic disease of chickens. Since 1949, preventive anticoccidials have been used but have not been totally effective. Losses due to morbidity from coccidiosis, including reduced weight gains and egg production, and decreased feed conversion, persist. The cost of coccidiosis in broiler production has been estimated at ½ to 1 cent per pound. Based on an annual production of 3,000,000,000 broilers annually in the United States, losses would total between 60 and 120 million dollars. To this figure must be added the cost of anticoccidials estimated at 35 million dollars. These impressive figures emphasize the importance of reducing the incidence of coccidiosis in chickens.

Of the nine genera of coccidia known to infect birds, the genus Eimeria contains the most economically important species. Various species of Eimeria infect a wide range of hosts, including mammals, but nine species have been recognized as being pathogenic to varying degrees in chickens: *Eimeria acervulina, E. mivati, E. mitis, E. praecox, E. hagani, E. necatrix, E. maxima, E. brunetti* and *E. tenella*.

Although the Eimeria are highly host specific, their life cycles are similar. The developmental stages of the avian coccidia can be illustrated by the species *Eimeria tenella*, which proliferates in the cecum of the chicken.

The life cycle of the Eimeria species begins when the host ingests previously sporulated oocysts during ground feeding or by inhalation of dust. Mechanical and chemical action in the gizzard and intestinal tract of the chicken ruptures the sporulated oocyst, liberating eight sporozoites. The sporozoites are carried in the digestive contents and infect various portions of the intestinal tract by penetration of epithelial cells. Subsequent life stages involve asexual multiple fission, the infection of other epithelial cells, development of gametes, and fertilization to produce a zygote which becomes an oocyst which is passed out of the host with the droppings. The oocyst undergoes nuclear and cellular division resulting in the formation of sporozoites, with sporulation being dependent upon environmental conditions. Ingestion of the sporulated oocyst by a new host transmits the disease.

Of all species of Eimeria, *E. tenella* has received the most attention. *E. tenella* is an extremely pathogenic species, with death often occurring on the fifth or sixth day of infection.

Before the use of chemotherapeutic agents, poultry producers' attempts to control coccidiosis were limited to various management programs. These programs were directed toward attempts at sanitation through disinfection, or by mechanical removal of litter. Despite these efforts, sufficient oocysts usually remained to transmit the disease.

One means of combating the hazards of coccidia is immunization. This method involves feeding to the poultry a small dose of oocysts of each of the species of coccidia during the first weeks of life. However, dosage control has proven difficult as birds ingest daughter oocysts, with some birds developing severe coccidiosis and others remaining susceptible. Also, since this procedure produces mixed infections, sometimes adequate immunity does not develop to all species given. In addition, immunity development is too slow for use with broiler production.

Another means of combating coccidia is drug treatment after the poultry is infected. One drug that has been used is sulfanilamide which has shown anticoccidial activity against six species of coccidia. However, unless the drug treatment of the flock is quickly initiated after diagnosis of the disease, medication may be started too late to be effective.

Ideally, the best method for combating coccidia is preventive medication. Since the advent of the use of sulfonamide drugs, over forty compounds have been marketed for preventive medication against coccidia. There have been many problems with the use of such drugs, including anticoccidial contamination of layer flock feeds, inclusion of excessive anticoccidial drugs in the feed causing toxicity in the birds and omission of the anticoccidial from the feed resulting in coccidiosis outbreaks. A particularly frustrating problem has been the development of drug-resistant strains of coccidia. Moreover, there is a potential for drug residues being deposited in the meat.

Clearly, available methods for the control of coccidiosis have met with limited success, and the need for a safe, efficient, and inexpensive method of combating avian coccidiosis remains.

The development of an effective anticoccidial vaccine is a desirable solution to the problem of disease prevention. Vaccines produced by traditional methods will require extensive development. There are reports of the production of attenuated strains through passage in embryos or cell culture. While this approach may eventually lead to successful birds, which react with a variety of different antigens and often with multiple determinants on a single antigen.

Alternate technology to the production of "subunit" or "synthetic" vaccines is the use of a fowl pox virus vector. The pox virus vaccinia has a long history of use as a vaccine and has been employed to virtually irradicate smallpox in humans. It now has been demonstrated that vaccinia virus can be effectively genetically engineered to express foreign antigens (Smith et al., *Nature* 302:490-495 (1983); Panicali et al., *Proc. Natl. Acad. Sci. U.S.A.* 80:5364-5368 (1983); Mackett et al., *J. of Virology* 49:857-864 (1984)) and the engineered viruses can serve as a live vaccine against other viruses and infections besides smallpox. Fowl pox virus is very similar to vaccinia virus and many of the methods developed for vaccinia for the creation of recombinants expressing foreign antigens can be applied to fowl pox. Attenuated fowl pox virus engineered to produce avian coccidia antigens thus is another method to produce an anticoccidial vaccine. Live vaccines have the advantage of being inexpensive to produce and are characterized by the production of rapid immunity development.

A second type of live vaccine results in the presentation of antigen in the gut where coccidia normally invades. This method utilizes secretion or outer surface expression of the antigen by harmless bacteria introduced into the intestinal microbial population by incorporation in feed. Secretion is obtained by fusion of an antigen gene to the gene coding for a protein which is normally secreted, leaving the necessary secretion signal sequence intact. Outer surface expression is achieved by vaccines, not all the important species of Eimeria have been adapted to growth in culture or embryos such that they are capable of completing their life cycle.

Genetic engineering methodology presents the opportunity for an alternative approach to vaccine development. It is known that genes encoding antigenic proteins of pathogenic organisms can be cloned into microorganisms. The antigenic proteins then can be expressed at high levels, purified, and used as vaccines against the pathogenic organism. These antigenic proteins have the advantage of being noninfectious and are potentially inexpensive to produce. Such "subunit vaccines" have been prepared from antigen genes for a number of viruses such as hepatitis, herpes simplex and foot and mouth disease virus. An alternate approach is to produce "synthetic vaccines", small chemically-synthesized peptides, whose sequence is chosen based upon the amino acid sequence translation of viral antigen DNA. The advantages of such "synthetic vaccines" over traditional vaccination with attenuated or killed pathogenic organisms have been summarized by Lerner in Nature 299:592-596 (1982).

It is now possible to produce foreign proteins, including eukaryotic proteins, in prokaryotic organisms such as gram positive or gram negative bacteria. The process involves the insertion of DNA (derived either from enzymatic digestion of cellular DNA or by reverse transcription of mRNA) into an expression vector. Such expression vectors are derived from either plasmids or bacteriophage and contain: (1) an origin of replication functional in a microbial host cell; (2) genes encoding selectable markers, and (3) regulatory sequences including a promoter, operator, and a ribosome binding site which are functional in a microbial host cell and which direct the transcription and translation of foreign DNA inserted downstream from the regulatory sequences. To increase protein production and stability, eukaryotic proteins are often produced in prokaryotic cells as a fusion with sequences from the amino-terminus of a prokaryotic protein. β-Galactosidase or the product of one of the *E. coli* tryptophan operon genes have been used successfully in this manner. Expression vectors have also been developed for expression of foreign proteins in eukaryotic host cells, e.g., yeast and chinese hamster ovary tissue culture cells.

Host cells transformed with expression vectors carrying foreign genes are grown in culture under conditions known to stimulate production of the foreign protein in the particular vector. Such host cell/expression vector systems are often engineered so that expression of the foreign protein may be regulated by chemical or temperature induction. Proteins which are secreted may be isolated from the growth media, while intracellular proteins may be isolated by harvesting and lysing the cells and separating the intracellular components. In this manner, it is possible to produce comparatively large amounts of proteins that are otherwise difficult to purify from native sources.

Such microbially produced proteins may be characterized by many well-known methods, including the use of monoclonal antibodies, hereinafter referred to as "MAbs," which are homogeneous antibodies that react specifically with a single antigenic determinant and display a constant affinity for that determinant, or by use of polyvalent antibodies derived from infected fusion of the antigen genes to the genes that code for proteins normally localized on the outer surface. (T. Silhavy, U.S. Patent No. 4,336,336.) This type of live vaccine is especially advantageous since manufacturing costs are minimal and the immune response stimulated is of a type particularly effective against coccidia invasion of the gut.

SUMMARY OF THE INVENTION

This invention relates to novel recombinant antigenic proteins of avian coccidiosis, and fragments thereof containing antigenic determinants, and to the genes that encode the antigenic peptides. It has now been found that particular polypeptides present in avian cells infected with coccidiosis, when purified and isolated, contain an antigenic determinant or determinants which can elicit an antibody response. This invention also relates to vaccines made using the novel antigenic proteins of avian coccidiosis and to methods of immunizing chickens against avian coccidia.

BRIEF DESCRIPTION OF THE FIGURES

FIGS. 1a and 1b show the nucleotide sequence of the 5'-3, strand of cDNA encoding the *E. acervulina* antigen ac-1b gene.

FIGS. 2a and 2b show the amino acid sequence of *E. acervulina* antigen ac-1b.

FIGS. 3a and 3b show the nucleotide sequence of the 5'-3, strand of cDNA encoding the *E. acervulina* antigen ac-6b gene.

FIGS. 4a and 4b show the amino acid sequence of *E. acervulina* antigen ac-6b.

FIG. 5 shows the nucleotide sequence of the 5'-3' strand of cDNA encoding the *E. tenella* antigen tc-7a gene.

FIG. 6 shows the amino acid sequence of *E. tenella* antigen tc-7a.

FIG. 7 shows the nucleotide sequence of the 5'-3' strand of cDNA encoding the E. tenella clone tc-8a gene.

FIG. 8 shows the amino acid sequence of *E. tenella* clone tc-8a.

FIG. 9 shows the nucleotide sequence of the 5'-3' strand of cDNA encoding the E. tenella antigen tc-10a gene.

FIG. 10 shows the amino acid sequence of *E. tenella* antigen tc-10a.

As is well known in the art, due to the degeneracy of the genetic code, the DNA sequences given in the Figures for the genes and antigenic peptides of this invention may be encoded by different DNA than those represented. Thus, knowledge of an amino acid sequence does not necessarily lead to a precise genetic sequence coding therefor. In all of the Figures with DNA and amino acid sequences the sequence is given as the 5' to 3' strand. The abbreviations have the following standard meanings:

A is deoxyadenyl
T is thymidyl
G is deoxyguanyl
C is deoxycytosyl
GLY is glycine
ALA is alanine
VAL is valine
LEU is leucine
ILE is isoleucine
SER is serine
THR is threonine
PHE is phenylalanine
TYR is tyrosine
TRP is tyryptophan
CYS is cysteine
MET is methionine
ASP is aspartic acid
GLU is glutamic acid
LYS is lysine
ARG is arginine
HIS is histidine
PRO is proline
GLN is glutamine
ASN is asparagine.

DETAILED DESCRIPTION OF THE PREFERRED EMBODIMENT

The present invention relates to recombinant antigenic proteins, and fragments thereof containing antigenic determinants, that can elicit an antibody response against avian coccidiosis, and to the cloned genes that encode the antigenic proteins and fragments. These antigenic proteins, and the fragments thereof containing antigenic determinants, will bind with a specific monoclonal antibody or with polyvalent antibodies from infected chickens, or from other animals that have been immunized with life forms of Eimeria or Eimeria proteins, directed against an antigenic protein of avian coccidia.

The antigenic proteins of this invention may be used for several applications: (1) the protein(s) can be used in an avian coccidia assay to detect antibodies against the coccidia; (2) antibodies may be prepared from the antigenic protein(s); (3) the protein(s) can be used for preparing vaccines against avian coccidiosis.

Antibodies directed against coccidial-antigens are used to identify, by immunological methods, transformed cells containing DNA encoding coccidial antigens. The MAbs are used as a tool for identifying cells containing DNA sequences encoding coccidial antigens that are either species specific or common to all nine species. Screening transformants with polyvalent chicken antiserum is used to identify DNA sequences encoding a wide spectrum of coccidial proteins which are antigenic in chickens upon infection. DNA sequences from the transformants thus identified then may be incorporated into a microorganism for large scale protein production. The antigenic proteins, as native proteins or as hybrids with other proteins, may be used as vaccines to immunize birds to protect them from subsequent infection.

In addition, the DNA sequences comprising the genes that encode antigenic proteins and fragments thereof may be used as DNA probes. The probes have a variety of uses, including screening a DNA library for additional genes that may encode antigenic determinants.

The DNA probe may be labeled with a detectable group. Such detectable group can be any material having a detectable physical or chemical property. Such materials have been well-developed in the field of immunoassays and in general almost any label useful in such methods can be applied to the present invention. Particularly useful are enzymatically active groups, such as enzymes (see *Clin. Chem.* 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); fluorescers (see Clin. Chem. 25:353 (1979)); chromophores; luminescers such as chemiluminescers and bioluminescers (see Clin. Chem. 25:512 (1979)); specifically bindable ligands; proximal interacting pairs; and radioisotopes such as $^3H$, $^{35}S$, $^{32}P$, $^{125}I$ and $^{14}C$. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the latter include, but are not limited to, betagalactosidase, alkaline phosphatase and peroxidase.

As used herein, the term "antigenic" or "antigenic determinant" is meant immunologically cross-reactive antigenic determinants with which a given antibody will react. Therefore, the antigenic peptides of this invention will include chemically synthesized peptides, peptides made by recombinant DNA techniques, and antibodies or fragments thereof which are anti-idiotypic towards the determinant of the peptides of this invention.

Several procedures may be used to construct a microorganism that produces an antigenic protein that binds with a monoclonal or polyvalent antibody that is directed against an antigenic protein of avian coccidia. One such procedure can be divided into the following major stages, each of which is described more fully herein: (1) recovery and isolation of messenger RNA (mRNA) found in organisms of the genus Eimeria; (2) in vitro synthesis of complementary DNA (cDNA), using coccicidia mRNA as a template; (3) insertion of the cDNA into a suitable expression vector and transformation of bacterial cells with that vector; and, (4) recovery and isolation of the cloned gene or gene fragment. This route is referred to as the mRNA route. The advantage to this route is that only "expressed" genes are cloned, reducing the number of individual transformants required to represent the entire population of genes.

An alternative procedure can be divided into the following major stages which will also be described more fully herein: (1) recovery and isolation of nuclear DNA found in organisms of the genus Eimeria; (2) fragmentation of the DNA and insertion into a suitable vector; (3) transformation into a suitable microbial host; (4) selection of transformants containing a gene which specifies the antigen of interest; and, (5) recovery and isolation of the cloned gene or gene fragment. This route is referred to as the nuclear DNA route. The advantage to this route is that all genes are cloned, allowing the identification of genes not expressed at the time from which mRNA is isolated. These may include genes which are expressed during stages of the life cycle which are not easy to isolate.

After recovery and isolation of the cloned gene that is derived from the procedures discussed above, the cloned DNA sequence is advantageously transferred to a suitable expression vector/host cell system for large scale production of the antigenic protein.

The DNA sequence that is to be isolated encodes an antigenic protein that will elicit an immune response when administered to chickens which will protect them from subsequent infections. It is not necessary to isolate a complete coccidial gene encoding such a protein, since those portions of the protein termed antigenic determinants are sufficient for triggering a protective immune response (Lerner, supra). This antigenic determinant should be on the surface of the folded microbially-produced protein to trigger the response (Lerner, supra).

In the mRNA route, the sequence may be isolated from the sporozoite life stage of the parasite. It has been demonstrated that part of the protective immune response in chickens is directed against the sporozoite. Scientists at the U.S. Department of Agriculture detected antibodies to sporozoite proteins in immune chicken serum, which also indicates that the sporozoite is a life stage that can be affected by an immune response in chickens. Antigenic proteins isolated from other life stages also may be effective as vaccines.

MAbs or polyvalent antibodies which bind to various sporozoite proteins can be used to identify cloned DNA sequences encoding those proteins. Such proteins can be isolated and used to elicit a protective immune response in chickens.

Sporozoites can be obtained from oocysts by excystation using the method of Doran and Vetterling, *Proc. Helminthol Soc. Wash.* 34:59-65 (1967), and purified by the leucopak filter technique of Bontemps and Yvore, *Ann. Rech. Vet.* 5:109-113 (1974). Although the method of Doran and Vetterling has been found suitable for obtaining sporozoites from oocysts, any method is suitable as long as the nucleic acids within the sporozoites remain intact. Also, sporozoite mRNA may be isolated from intact sporulated oocysts, which contain the sporozoites.

mRNA Route

Isolation of mRNA coding for the antigenic proteins of interest is advantageously accomplished by lysis of intact sporulated oocysts under conditions which minimize nuclease activity. This is accomplished using a modification of the procedure described by Pasternak et al., *Molec. Biochem. Parisitol.* 3:133-142 (1982). Total RNA may be isolated by grinding the oocysts with glass beads in a solution containing sodium dodecyl sulfate (SDS) and proteinase K. After denaturation and degradation of oocyst proteins, the RNA is isolated by extraction of the solution with phenol and precipitation with ethanol. Oligo (dT)-cellulose chromatography then can be used to isolate mRNA from the total RNA population.

Proteins coded for by the isolated mRNA can be synthesized, in vitro, using a cell-free translation system. A number of cell-free translation systems have been devised, such as wheat germ extract (Martial et al., *Proc. Nat'l Acad. Sci. U.S.A.* 74:1816-1820 (1977)), rabbit reticulocyte lysate (Pelham and Jackson, *Eur. J. Biochem.* 67:247-256 (1976)), and oocytes from *Xenoous laevis* (Sloma et al., *Methods in Enzymology* 79:68-71 (1981)). The rabbit reticulocyte lysate is preferred for the testing of sporozoite mRNA. The rabbit reticulocyte lysate can be supplemented with a radioactively labeled amino acid, such as [$^{35}$S]-methionine, so that the resulting proteins contain a tracer. The various protein products may be reacted with polyvalent chicken antisera or MAbs previously described, followed by reaction with goat anti-chicken IgG in the case of the polyvalent antibodies and *Staphylococcus aureus* Protein A, or in the case of the MAbs, just Protein A. Protein A binds any of the mouse or goat antibodies to form an immuno-precipitated complex. The products of the translation and of the immunoprecipitation are visualized by gel electrophoresis followed by fluorography. The mRNA fractions found to produce proteins that react with the antisera in this system are used for ds-cDNA synthesis. Alternatively, to avoid missing any antigens which are not synthesized efficiently, in vitro, or are not immuno-precipitated efficiently, total mRNA is used for cDNA synthesis.

Synthesis of cDNA employs avian myeloblastosis virus reverse transcriptase. This enzyme catalyzes the synthesis of a single strand of DNA from deoxynucleoside tri-phosphates on the mRNA template. (Kacian and Myers, *Proc. Nat'l Acad. Sci. U.S.A.* 73:2191-2195 (1976).) The poly r(A) tail of mRNA permits oligo(dT) (of about 12-18 nucleotides) to be used as a primer for cDNA synthesis. The use of a radioactively labeled deoxynucleoside triphosphate facilitates monitoring of the synthesis reaction. Generally, a $^{32}$p-containing deoxynucleoside triphosphate, such as [$\alpha$-$^{32}$P]dCTP, may be used advantageously for this purpose. The cDNA synthesis is generally conducted by incubating a solution of the mRNA, the deoxynucleoside triphosphates, the oligo(dT)12-18 and reverse transcriptase for 10 minutes at 46° C. The solution also preferably contains small amounts of actinomycin D and dithiothreitol to promote full length synthesis. (Kacian and Myers, supra.) After incubation, ethylenediaminetetraacetic acid (EDTA) is added to the solution, and the solution is extracted with phenol:chloroform. The aqueous phase is advantageously purified by gel filtration chromatography, and the cDNA-mRNA complex in the eluate is precipitated with alcohol.

The mRNA can be selectively hydrolyzed in the presence of the cDNA with dilute sodium hydroxide at an elevated temperature. Neutralization of the alkaline solution and alcohol precipitation yields a single-stranded cDNA copy.

The single-stranded cDNA copy has been shown to have a 5' poly (dT) tail, and to have a 3' terminal hairpin structure, which provides a short segment of duplex DNA. (Efstratiadis et al., Cell 7:279-288 (1976)). This 3, hairpin structure can act as a primer for the synthesis of a second DNA strand. Synthesis of this second strand is conducted under essentially the same conditions as the synthesis of the cDNA copy, except that the Klenow fragment of *E. coli* DNA polymerase I (Klenow et al., *Eur. J. Biochem.* 22:371-381 (1971)) is substituted for reverse transcriptase. The duplex cDNA recovered by this procedure has a 3' loop, resulting from the 3' hairpin structure of the single-stranded cDNA copy. This 3' loop can be cleaved by digestion with the enzyme, S1 nuclease, using essentially the procedure of Ullrich et al., *Science* 196:1313-1319 (1977). The S1 nuclease digest may be extracted with phenol-chloroform, and the resulting ds-cDNA precipitated from the aqueous phase with alcohol.

For purposes of amplification and selection, the ds-cDNA prepared as described above is generally inserted into a suitable cloning vector, which is used for transforming appropriate host cells. Suitable cloning vectors include various plasmids and phages, but a bacteriophage lambda is preferred.

For a cloning vector to be useful for the expression of foreign proteins which are to be detected with antibodies, it should have several useful properties. Most importantly, it should have a cloning site within a gene which is expressed in the host being used. There should also be a means of controlling expression of the gene. The vector should be able to accept DNA of the size required for synthesis of the desired protein product and replicate normally. It is also useful to have a selectable property which allows identification of vectors carrying inserts. A cloning vector having such properties is the bacteriophage λgt11 (ATCC 37194) (Young and Davis, *Proc. Nat'l Acad. Sci. U.S.A.* 80:1194-1198 (1983)). This vector has a unique EcoRI site near the end of the bacterial gene coding for β-galactosidase. That site can be used for insertion of foreign DNA to make hybrid proteins made up of β-galactosidase and the foreign gene product. The expression of β-galactosidase is under control of the lac promoter and can be induced by the addition of isopropyl-α-D-thiogalactopyranoside (IPTG). The λgt11 phage contains 43.7 kb of DNA which is considerably smaller than wild type λ. This allows insertion of pieces of DNA up to 8.3 kb in length, before the DNA becomes too large to fit inside the phage head. Because DNA is inserted into the gene for β-galactosidase, transformants having inserts can easily be distinguished from those which do not by looking for β-galactosidase activity. An indicator dye, 5-bromo-4-chloro-3-indolyl-β-D-galactoside (Xgal), can be incorporated with agar plates. β-galactosidase cleaves this molecule to give a blue product, thus allowing examination of the cultures for the presence of active β-galactosidase. Those plaques having inserts are colorless on X-gal plates because the insertion of foreign DNA into the β-galactosidase gene has eliminated its activity.

The ds-cDNA can be conveniently inserted into the phage by addition of EcoRI linkers to the DNA and ligation into the EcoRI-cut λgt11 DNA. After ligation of the cDNA into the phage DNA, the DNA is packaged, in vitro, into λ phage heads (Enquist and Sternberg, *Methods in Enzymology* 68:281-298 (1979) and those phages are used to infect a suitable λ-sensitive host. With the proper choice of host, the phage may be screened as plaques or lysogens (colonies).

Aside from the *E. coli*/bacteriophage λgt11 system described, many other host/vector combinations have been used successfully for the cloning of foreign genes in *E. coli* (Principles of Gene Manipulation, 2nd Ed., Old and Primrose, Univ. of California Press, 32-35, 46-47 (1981)) including "open reading frame" vectors, described in detail later.

The foregoing discussion has focused on cloning procedures in gram negative bacteria, e.g., *E. coli*. Alternatively, foreign genes may be cloned into plasmid vectors that will transform and replicate in a gram positive bacterium such as *Bacillus subtilis* (Old and Primrose, supra, pp. 51-53) or in a eukaryotic host cell such as yeast (Old and Primrose, supra, pp. 62-68) filamentous fungi, insect cells (U.S. Pat. Nos. 4,745,051 and 4,879,236) and mammalian cells. Cloning vectors have been constructed which transform both yeast and *E. coli*. Such vectors are termed "shuttle vectors" and may be transferred, along with the cDNA they carry, between the two host microorganisms (Storms, et al., *Journal of Bacteriology* 140:73-82 (1979); and Blanc et al., *Molec. Gen. Genet.* 6:335-342 (1979). Shuttle vectors also exist which replicate in (and may carry cloned genes into) both *E. coli* and *B. subtilis* (Old and Primrose, supra, at p. 53). Vectors derived from the other bacteriophages such as M13 have also proven useful in the cloning of foreign genes (Old and Primrose, supra, Chap. 5). Any of these techniques can be employed, if desired, in the constructions of the present invention.

The DNA described herein may be inserted into the above vectors by various techniques including homopolymeric tailing, blunt-end ligation or by use of linker molecules (Old and Primrose, supra, at p. 92).

Many immunological methods for screening clone banks for those expressing a desired protein are known and include procedures described by Engvall and Pearlman, *Immunochemistry* 8:871-874 (1971); Koenen et al., *The European Molecular Biology Organization Journal*, Vol. 1, No. 4, pp. 509-512 (1982); Broome et al., *Proc. Natl. Acad. Sci., U.S.A.* 75:2746-2749 (1978); Villa-Komaroff et al., *Proc. Natl. Acad. Sci., U.S.A.* 5:3727-3731 (1978); Anderson et al., *Methods in Enzymology* 68:428-436 (1979); Clarke et al., *Methods in Enzymology* 68:436-442 (1979); Ehrlich et al., *Methods in Enzymology* 68:443-453 (1979); Kemp et al., *Proc. Natl. Acad. Sci., U.S.A.* 78:4520-4524 (1981).

By the cloning procedures outlined, thousands of recombinant bacteriophage are generated. In order to screen them for production of coccidial antigens, two antibody screens can be utilized. Both screening methods depend upon expression of the coccidial antigenic protein either alone or as a fusion protein with a bacterial gene. In the examples included herein, the coccidial antigens are produced as fusions with *E. coli* β-galactosidase. The screening methods, therefore, depend on expression of the fusion product and detection of the product by reaction with antibodies, either monoclonal or polyvalent, directed against that antigen.

The recombinant bacteriophages can be used to infect a suitable *E. coli* host which allows the formation of phage plaques on agar (or agarose) plates. The plaques can be transferred to nitrocellulose membranes while being induced with IPTG. The proper antibodies are then reacted with the filters. After reaction of the primary antibodies with the filters, the positive reactions are detected by reaction with either [$^{125}$I]*Staphylococcus aureus* Protein A or a second antibody conjugated with horseradish peroxidase.

Alternatively, the recombinant bacteriophages can be used to infect an *E. coli* host in which lysogens are produced at a high frequency. In this case, the transformants can be screened as colonies. The colonies are grown on a cellulose acetate filter under non-induced conditions. After the colonies have reached a suitable size, the cellulose acetate filter is placed over a nitrocellulose filter which is on an agar plate containing IPTG. The colonies are incubated at elevated temperatures to induce phage production, while expression of the β-galactosidase gene is induced by inclusion of IPTG. After a suitable incubation period, during which some lysis of the colonies occurs with release of proteins through the cellulose acetate filter onto the nitrocellulose filter, the cellulose acetate filter is removed. The nitrocellulose filter is processed as described above for screening of plaques.

The phages giving positive signals in the antibody-screening procedure can be shown to contain sequences coding for coccidial proteins by excision of the DNA originally inserted into the phage DNA and examination of the ability of that DNA to hybridize with coccidia mRNA or coccidia genomic DNA. The nucleotide sequence of the cDNA insert is determined using the methods of Sanger et al., *Proc. Natl. Acad. Sci., U.S.A.* 74:5463-5467 (1977); or Maxam and Gilbert, *Proc. Natl. Acad. Sci., U.S.A.* 74:560-S64 (1977).

Nuclear DNA Route

Another method of cloning coccidial antigens begins with isolation of nuclear DNA from oocysts. This DNA is then broken into fragments of a size suitable for insertion into a cloning vector. To obtain such fragments, one can use mechanical shearing methods such as sonication or high-speed stirring in a blender to produce random breaks in the DNA. Intense sonication with ultrasound can reduce the fragment length to about 300 nucleotide pairs. (Old and Primrose, supra, p. 20.) Alternatively, nuclear DNA may be partially digested with DNAseI, which gives random fragments, with restriction endonucleases, which cut at specific sites, or with mung bean nuclease in the presence of formamide, which has been shown with some related organisms (McCutchan, T. F., et al. *Science* 225:625-628 (1984)) to produce DNA fragments containing intact genes.

These nuclear DNA fragments may be inserted into any of the cloning vectors listed for the cloning of cDNA in the mRNA experimental method. If the nuclear DNA is digested with a restriction endonuclease, it can be inserted conveniently into a cloning vector digested with the same enzyme, provided the vector has only one recognition site for that enzyme. Otherwise, DNA fragments may be inserted into appropriate cloning vectors by homopolymeric tailing or by using linker molecules (Old and Primrose, supra, at p. 92).

Advantageously, the nuclear DNA fragments are cloned into "open reading frame" vectors which are designed to simultaneously clone and express foreign genes or fragments thereof. Several such vectors are known in the art, including those described by Weinstock et al., *Proc. Natl. Acad. Sci., U.S.A.* 80:4432-4436 (1983); Keonen et al., *The European Molecular Biology Organization Journal* 1, 4, pp. 509-512 (1982); Ruther et al., 79:6852-6855 (1982); Young and Davis, supra; and Gray et al., *Proc. Natl. Acad. Sci., U.S.A.* 79:6598-6602 (1982).

Open reading frame (ORF) vectors have been used to clone both prokaryotic and eukaryotic genomic DNA or cDNA. These vectors generally contain a bacterial promoter operably linked to an amino terminal fragment of a prokaryotic gene. A carboxy terminal fragment of a gene which encodes a product for which an assay is known (e.g., the *E. coli* lacZ gene which encodes β-galactosidase) is located downstream. The sequences between the amino terminal gene fragment and the lacZ fragment include restriction endonuclease recognition sites useful for insertion of foreign genes and, in some cases, also place the lacZ fragment out of reading frame for translation with respect to the amino terminal gene fragment When foreign DNA is inserted into these vectors (by blunt end ligation, homopolymeric tailing, ligation of cohesive termini, or the use of linkers), a certain percentage of recombinants will have received foreign DNA of a length that puts the lacZ gene in phase with the reading frame set by the amino terminal gene fragment. The result is production of a "tribrid" protein comprising the polypeptides encoded by the amino terminal gene fragment, the cloned DNA, and the lacZ gene. Such recombinants are identified on MacConkey agar plates or on agar plates containing "Xgal" (5-bromo-4-chloro-3-indolyl-β-D galactoside) because the β-galactosidase activity of the tribrid protein cleaves the dye in such plates, turning colonies red (MacConkey agar) or blue (Xgal). β-galactosidase can carry a wide range of protein sequences at its amino terminus and still retain biological activity. Alternatively, the insert may be inserted to inactivate a gene by interrupting the sequence. The insert may be in the correct reading frame to produce a hybrid gene consisting of the amino-terminus of the bacterial gene and sequences from the insert gene at the carboxy terminus.

Only recombinants receiving exons (i.e., coding sequences of genes, which have no stop codons) which are in-frame with respect to the amino terminal gene fragment are detected by this method. ORF vectors are useful for cloning genes for which no DNA or protein sequence data exists, if antibodies against the gene product exist. Screening of the clone bank may be accomplished by immunological methods which make RNA or DNA hybridization probes unnecessary. The immunological screening methods mentioned for the mRNA route can be used.

Plasmid DNA is isolated from transformants found to be "positive" by the above screening methods. The nuclear DNA inserts of these plasmids are then subjected to DNA sequencing. Once the nucleotide sequence is known, it is possible by known methods to chemically synthesize all or part of the cloned coccidial genes. The synthesis of fragments of the cloned genes, followed by insertion of the gene fragments into expression vectors as described below and reaction of the polypeptides produced with MAbs allows detection of those portions of the gene which are antigenic determinants.

Once a cloned DNA sequence is identified as encoding a protein that binds antibodies directed against coccidial proteins, it may be transferred to expression vectors engineered for high-level production of the desired antigenic protein. The expression vectors are transformed into suitable host cells for production of the antigenic protein. These host cells may include both prokaryotic and eukaryotic organisms.

The prokaryotic host cells include *E. coli* and *B. subtilis*. The eukaryotic host cells include yeast, insect cells, and mammalian cells.

Coccidial antigens advantageously may be produced at high levels in *E. coli* as a fusion protein comprising the antigen and an amino terminal portion of the β-subunit of the enzyme tryptophan synthetase (the product of the *E. coli* troB gene). This fusion is accomplished by inserting a DNA sequence encoding a coccidial antigen into a plasmid vector carrying the trpB gene.

The expression vector used may be one in which expression of the fusion antigenic protein is highly regulatable, e.g., by chemical induction or temperature changes. An expression vector with such regulatory capability is the plasmid pGX2606, which contains a hybrid $\lambda O_L P_R$ regulatory region as described in copending application Ser. No. 534,982 filed Sep. 23, 1983 Host expression vector systems in which expression of foreign proteins is regulatable have the advantage of avoiding possible adverse effects of foreign protein accumulation as high cell densities are reached. Some investigators have proposed that expression of gene fragments such as those encoding antigenic determinants may avoid the deleterious effects that expression of the entire antigenic protein would have on *E. coli* host cells. (Helfman et al., *Proc. Natl. Acad. Sci., U.S.A.* 80:31-35 (1983)).

Coccidial antigens also may be produced in high levels as fusions at the carboxy-terminal of *E. coli* β-galactosidase, as they are directly obtained by use of the cloning vector λ-gt11. The fused β-galactosidase-coccidia antigen gene is transferred with all of the associated regulatory elements to a small plasmid, where synthesis of the gene product is regulated by the lac promoter, which is transferred along with the fusion gene from the phage to the plasmid. Such a small plasmid is PGX1066 (plasmid pGX1066 is present in *E. coli* strain GX1186, ATCC 39955) which carries the gene for ampicillin resistance and has a bank of restriction sites which are useful for insertion of DNA fragments. Synthesis of the fusion protein is induced by addition of IPTG, the inducer of the lac operon.

An effective subunit vaccine against avian coccidiosis may consist of a mixture of antigen proteins derived from several species of Eimeria. Alternatively, production costs may be decreased by producing two or more antigen proteins as one fusion protein thus reducing the required number of fermentations and purifications. Such a fusion protein would contain the amino acid sequence comprising an antigenic epitope of each antigen protein (or repetitions of those sequences) with variable amounts of surrounding nonantigenic sequence. A hybrid gene designed to code for such a protein in *E. coli* would contain bacterial regulatory sequence (promoter/operator) and the 5' end of an *E. coli* gene (the ribosome binding site and codons for several amino acids) to ensure efficient translation initiation followed by the coding sequences for the antigenic epitopes all fused in the same reading frame.

*E. coli* cells transformed with the expression vector carrying a cloned coccidial antigen sequence are grown under conditions that promote expression of the antigenic polypeptide. The antigenic protein is then purified from the cells and tested for ability to elicit an immune response in chickens that will protect them from subsequent Eimeria infections. The purified protein may be used to immunize the birds. The purified protein may be combined with suitable carriers and adjuvants and administered to birds in their feed or by injection. Alternatively, live microorganisms containing the DNA sequences encoding the coccidial antigens may be fed to chickens. Such microorganism are advantageously those which normally inhabit the avian intestinal tract, such as *E. coli* or coryneform bacteria.

In a preferred system, the microorganisms are transformed with an expression vector in which the sequences encoding the coccidial antigen are fused in frame to a gene or gene fragment encoding a host cell outer membrane protein or secreted protein, such as the *E. coli* lamB protein, the λ receptor. The antigenic protein is therefore continuously presented in the host at the location of infection by the parasites. It is known that foreign proteins fused in expression vectors to outer membrane or secreted proteins have been presented at the cell surface or secreted from their host cells. (Weinstock, supra, and Silhavy, U.S. Pat. No. 4,336,336 which is herein incorporated by reference.)

In another preferred system for development of live vaccines, an attenuated fowl pox virus expression vector is utilized. Fowl pox has the capacity to accommodate several coccidia genes allowing the production of multivalent vaccines. Currently, attenuated fowl pox virus is utilized as a vaccine to protect commercial flocks against fowl pox infection. Virus preparation and treatment of birds with fowl pox virus genetically engineered to produce coccidia antigens is the same as the conventional methods of pox vaccine use currently practiced.

Pox viruses are among the most complex viruses known with very high molecular weight double-stranded DNA genomes. With the most studied pox virus, vaccinia, it has been demonstrated that the pox genome can easily accommodate inserts of foreign DNA capable of coding for foreign antigenic proteins (Smith et al., supra; Panicali et al., supra; Mackett et al., supra). When a foreign gene is incorporated into the pox virus genome under the control of a pox promoter regulatory sequence, the foreign antigen is expressed upon infection in the cytoplasm of the cell where the pox virus replicates. Successful insertion and expression of coccidia antigen genes within the fowl pox genome is dependent upon identifying a nonessential region of the pox DNA for antigen gene insertion and ensuring an active pox promoter is situated 5' of the desired coccidia gene.

Insertion of DNA into the pox genome is accomplished by in vivo recombination. Pox DNA is not infectious presumably because its cytoplasmic location requires the presence of pox virus specific RNA and DNA polymerases that are normally carried into the cell by the virion. DNA sequence information from vaccinia virus (Weir and Moss, *J. of Virology* 46:530-537 (1983); Venkatesan et al., *Cell* 125:805-813 (1981)) demonstrates sequence patterns in regulatory regions that are likely to be unique to vaccinia genes and thus not recognized by cellular enzymes. Because into the fowl pox genome is accomplished by in vivo recombination as has been demonstrated with vaccinia to occur at high frequency (Weir et al., *Proc. Natl. Acad. Sci., U.S.A.* 79:1210-1214 (1982)). A fowl pox virus infection of chick embryo fibroblasts is followed by transfection using the $CaCl_2$ precipitation technique (Graham et al., *Virology* 52:456-457 (1973); Stow et al., *J. Virology* 28:6182-192 (1978)) with plasmid DNA that includes the coccidia antigen gene placed under the control of a promoter functional in fowl pox, and DNA sequence homology with fowl pox. During the course of the infection recombination occurs. If a coccidia DNA sequence is inserted within the fowl pox homologous sequence on the transfected plasmid, upon recombination the coccidia DNA sequence is, in some cases, inserted into the pox virus genome. The infected cells and virus from a recombination attempt are harvested and fresh chick embryo fibroblast cells grown as a monolayer in tissue culture are infected at a low multiplicity such that individual plaques resulting from an initial single virus infection can be identified using conventional techniques. Desired recombinant viruses are identified using an in situ hybridization technique (Villarreal and Berg, *Science* 196:183-185 (1977)) using radioactive coccidia DNA sequence as probe. Alternatively, Viral DNA immobilized on nitrocellulose paper prepared from cells infected by plaque purified virus or cells infected with pools of potential recombinant viruses can be used for identification of desired recombinant viruses. Immunological screening of fixed cells (Greme et al., *Science* 228:737-740 (1985)) is an alternative to hybridization.

The region of fowl pox DNA included in the plasmid vector must be from a nonessential region, and is chosen by randomly testing segments of fowl pox DNA for regions that allow recombinant formation without seriously affecting virus viability using the method described above. Fowl pox DNA is purified (Muller et al., *J. Gen. Virology* 38:135 (1977); Gafford et al., *Virology* 89:229 (1978)), randomly sheared to about 3 kilobases and cloned into a small bacterial plasmid, such as pGx1066, creating several different isolates. Foreign DNA must be inserted into the fowl pox portion of the plasmids before testing the effect of recombination upon virus viability. To accomplish this, *E. coli* transposon insertions such as $\lambda\delta$ (Guyer, *Methods in Enzymology* 101:362-369 (1983)) can be readily placed within the fowl pox portion of the plasmid. Cotransfections that result in viable fowl pox recombinants containing sequence identify desirable nonessential fowl pox DNA for use in cotransfection plasmids.

Fowl pox DNA regions with partial sequence homology to the thymidine kinase gene of vaccinia identified by hybridization experiments are also useful for inclusion in the cotransfection plasmid since the thymidine kinase gene of vaccinia has been shown to be nonessential (Weir (1982), supra; Mackett et al., *Proc. Natl. Acad. Sci., U.S.A.* 79:4927-4931 (1982); Hruby and Ball, *J. Virology* 43:403-408 (1982)).

Placement of the coccidia antigen gene under the control of a fowl pox promoter is carried out by conventional in vitro manipulation of the plasmid before concurrent transfection and fowl pox infection. Promoter sequences useful for driving expression of the coccidia antigens could be identified by determination of the DNA sequence located 5' to fowl pox genes. Promotor sequences are then synthesized chemically and included in the plasmid vector adjacent to endonuclease cloning sites within the fowl pox homologous region of the plasmid. Putative promoter sequences identified through DNA sequencing of vaccinia DNA (Venkatesan et al. (1981), supra; Weir and Moss (1983), supra) are also chemically synthesized and compared with fowl pox promoters for optimal effect. Putative fowl pox promoters are verified by cloning them 5' of a test gene with an easily measured translation product such as chloramphenicol acetyltransferase (Gorman et al., *Molecular and Cellular Biology* 2:1044-1057 (1982)) in a bacterial plasmid. The plasmid is used to transfect fowl pox infected tissue culture cells and the cells are assayed for transient expression of the test gene.

Vaccinia virus has a broad host range and does infect chickens. Thus the vectors and methods already developed for vaccinia could be utilized to develop vaccines for avian coccidia and coccidiosis in any other genus included in the vaccinia host range. This approach requires caution since vaccinia is severely pathogenic to a small proportion of the human population.

A good alternative to pox vectors would be to utilize a herpes virus such as Marek's Disease virus or Herpes virus of turkeys. Attenuated forms of both viruses are currently used as live vaccines to prevent Marek's disease in poultry. Similar to pox viruses, herpes viruses have large double stranded DNA genomes and are good candidates for genetic engineering using in vivo recombination methods similar to those developed for vaccinia. The advantage of engineering Marek's disease virus to also provide protection against coccidia infection is that coccidia protection is provided at no additional production cost above the Marek's Disease Vaccine that is already generally in use.

The production of coccidia antigen by fowl pox recombinants is verified by immunological analysis of the protein produced in chick embryo fibroblast tissue culture cells after infection and also by testing the circulating antibody of birds infected with recombinant fowl pox virus for cross reaction with whole coccidia or protein isolated from coccidia of the appropriate species.

The cloned antigenic proteins used in vaccines above are tested for their ability to elicit an immune response in chickens that protects the birds from subsequent infection by any of the important species of Eimeria, including *E. tenella, E. acervulina, E. brunetti, E. mivati, E. maxima, E. praecox, E. mitis,* and *E. necatrix*. The cloning procedures described above may be repeated until DNA sequences encoding coccidial antigens that collectively protect chickens against coccidiosis are isolated and used as a vaccine by the methods above.

In addition to cloned antigenic proteins which may be useful as vaccines to protect against coccidiosis, another useful alternative which may be derived from cloning antigen genes is the use of small, synthetic peptides in vaccines (see Lerner, supra). After the sequence of antigenic proteins is determined, it is possible to make synthetic peptides based on that sequence. The peptides are conjugated to a carrier protein such as hemocyanin or serum albumin and the conjugate then can be used to immunize against coccidia.

It is contemplated that the procedures described may also be used to isolate antigenic proteins from other coccidia species that can be used in vaccines to protect other domestic animals from coccidiosis.

The following examples are supplied in order to illustrate, but not limit, the present invention.

EXAMPLE 1

Identification of an *Eimeria acervulina* cDNA Clone Encoding Antigen ac-Ib with a Monoclonal Antibody In order to identify antigens of *Eimeria acervulina*, expression libraries were prepared in lambda vector, $\lambda$gt11, using cDNA prepared from polyA mRNA isolated from *E. acervulina* oocysts. The methods used for construction of the libraries is described in Genex Patent Application, PCT/U.S. Pat. No. 89/02918, incorporated herein by reference. The cDNA expression library was screened with monoclonal antibody (MCA) 12-09 which was raised against the sporozoite stage of *E. acervulina*. The MCA was obtained from Dr. Harry Danforth, U.S. Department of Agriculture, Beltsville, Md.

The library to be screened was plated on a host that allows lysis and plaque formation. During induction of the antigens encoded by the phage, the plaques were transferred to nitrocellulose filters. Phage that produce antigens cross-reactive with MCA 12-09 were identified by screening the filters with MCA 12-09. The cDNA inserts from the MCA 12-09 positive phage were cloned into bacteriophage M13 and subjected to sequence analysis. Following sequence analysis, *E. acervulina* antigen ac-1b was identified. The complete sequence of ac-1b and its 25 Kd translation product are given in FIGS. 1a and 1b and 2a and 2b.

Antigens ac-1b was expressed in *E. coli* after insertion into the plasmid expression vector pEX-32b. Antigen ac-1b is encoded in expression vector pGX5361 and is expressed as a fusion protein with 11 Kd of the MS-2 polymerase under control of the $P_L$ promoter. The host strain pop2136 contains a temperature sensitive repressor of $P_L$ and expression of the fusion protein is fully induced at 42° C.

EXAMPLE 2

Identification of an *Eimeria acervulina* cDNA Clone Encoding Antigen ac-6b with a Monoclonal Antibody Using the techniques described in Example 1 *E. acervulina* libraries were screened with MCA 12-09. Phage that produce antigens crossreactive with the monoclonal were identified. The cDNA inserts from the MCA 12-09 positive phage were cloned into bacteriophage M13 and subjected to sequence analysis. Following sequence analysis, *E. acervulina* antigen ac-6b was identified.

Antigen ac-6b showed sequence homology to the carboxy terminal sequence of *E. tenella* antigen GX3262, which has been shown to be protective against Eimeria infections in chickens (Miller et al., *Infect. Immun.* 57:2014-2020 (1989), Danforth et al., *Poultry Sci.* 68:1643-1652 (1989). In order to recover the entire ac-6b gene, an *E. acervulina* cDNA expression library was screened with an 18 bp oligonucleotide corresponding to the extreme 5'-sequence of the original ac-6b sequence. A plaque that hybridized to the oligonucleotide was identified and shown by sequence analysis to contain the complete ac-6b gene which encodes a 21.6 Kd coccidial peptide. The sequence of ac-6b and its translation product is given in FIGS. 3a and 3b and 4a and 4b.

Antigen ac-6b was expressed in *E. coli* after insertion into the plasmid expression vector pEX-32b. Antigen ac-6b is encoded in expression vector pGX5368 and is expressed as a fusion protein with 11 Kd of the MS-2 polymerase under control of the $P_L$ promoter. The host strain pop2136 contains a temperature sensitive repressor of $P_L$ and expression of the fusion protein is fully induced at 42° C.

EXAMPLE 3

Identification of an *Eimeria tenella* cDNA Clone Encoding Antigen tc-7a with a Monoclonal Antibody In order to identify antigens of *Eimeria tenella*, expression libraries were prepared in the lambda vector, λgt11, using cDNA prepared from polyA mRNA isolated from *E. tenella* oocysts. The cDNA expression library was screened with monoclonal antibody (MCA) 12-07 which was raised against the sporozoite stage of *E. tenella*. The MCA was obtained from Dr. Harry Danforth, U.S. Department of Agriculture, Beltsville, Md.

The library to be screened was plated on a host that allows lysis and plaque formation. During induction of the antigens encoded by the phage, the plaques were transfer to nitrocellulose filters. Phage that produce antigens cross-reactive with MCA 12-07 were identified by screening the filters with MCA 12-07. The cDNA inserts from the MCA 12-07 positive phage were cloned into bacteriophage M13 and subjected to sequence analysis. Following sequence analysis, *E. tenella* antigen tc-7a was identified. Antigen tc-7a consists of an open reading frame of 540 bp that encodes the carboxy terminal fragment of the *E. tenella* protein. The DNA sequence of tc-7a and its 16.6 Kd translation product are shown in FIGS. 5 and 6.

Antigen tc-7a was expressed in *E. coli* after insertion into the plasmid expression vector pEX-32b. Antigen tc-7a is encoded in expression vector pGX5391 and is expressed as a fusion protein with 11 Kd of the MS-2 polymerase under control of the $P_L$ promoter. The host strain pop2136 contains a temperature sensitive repressor of $P_L$ and expression of the fusion protein is fully induced at 42° C.

EXAMPLE 4

Identification of an *Eimeria tenella* cDNA Clone Encoding Antigen tc-8a with a Monoclonal Antibody As described in Example 3, *E. tenella* libraries were screened with MCA 12-07. Phage that produce antigens crossreactive with the monoclonal were identified. The cDNA inserts from the MCA 12-07 positive phage were cloned into bacteriophage M13 and subjected to sequence analysis. Following sequence analysis *E. tenella* antigen tc-8a was identified.

Antigens tc-8a is encoded on a short DNA fragments of 117 bp. The fragment consists of an open reading frame covering its entire length. The DNA sequence of the fragment and its 3.5 Kd translation product is shown is FIGS. 7 and 8.

EXAMPLE 5

Identification of an *Eimeria tenella* cDNA Clone Encoding Antigen tc-10a with a Monoclonal Antibody As described in Example 3, *E. tenella* libraries were screened with MCA 12-07. Phage that produce antigens cross-reactive with the monoclonal were identified. The cDNA inserts from the MCA 12-07 positive phage were cloned into bacteriophage M13 and subjected to sequence analysis. Following sequence analysis, *E. tenella* antigen tc-10a was identified.

Antigens tc-10a is encoded on a short DNA fragments of 228 bp. The fragment consists of an open reading frame covering its entire length. The DNA sequence of the fragment and its 7.8 Kd translation product is shown is FIGS. 9 and 10.

While certain representative embodiments and details have been shown for the purpose of illustrating the invention, it will be apparent to those skilled in the art that various changes and modifications may be made therein without departing from the scope of the invention.

What is claimed is:

1. A cloned DNA molecule encoding antigen ac-66 consisting essentially of the nucleotide sequence as shown in FIG. 3.

2. An expression vector comprising the nucleotide sequence of claim 1, under the control of a regulatory region capable of directing expression of said nucleotide sequence.

3. The expression vector of claim 2 wherein said vector is selected from the group consisting of plasmids, bacteriophages, viruses.

4. A host cell or organism transformed by the expression vector of claim 1 selected from the group consisting of bacteria, yeast, fungi, insect, and mammalian cells.

* * * * *